(12) United States Patent
Lo

(10) Patent No.: US 11,357,729 B2
(45) Date of Patent: Jun. 14, 2022

(54) METHOD FOR ADMINISTERING SOLID WATER PARTICLES TO PREVENT BACTERIA GROWTH IN LIVING ORGANISMS

(71) Applicant: Shui Yin Lo, Arcadia, CA (US)

(72) Inventor: Shui Yin Lo, Arcadia, CA (US)

( * ) Notice: Subject to any disclaimer, the term of this patent is extended or adjusted under 35 U.S.C. 154(b) by 0 days.

(21) Appl. No.: 16/843,410

(22) Filed: Apr. 8, 2020

(65) Prior Publication Data

US 2020/0330387 A1 Oct. 22, 2020

Related U.S. Application Data

(60) Provisional application No. 62/836,940, filed on Apr. 22, 2019.

(51) Int. Cl.
*A61K 9/14* (2006.01)
*A61K 9/00* (2006.01)
*A61K 33/00* (2006.01)

(52) U.S. Cl.
CPC .............. *A61K 9/14* (2013.01); *A61K 9/0014* (2013.01); *A61K 9/0053* (2013.01); *A61K 33/00* (2013.01)

(58) Field of Classification Search
None
See application file for complete search history.

(56) References Cited

U.S. PATENT DOCUMENTS

| 2013/0085137 A1* | 4/2013 | Grigorian | A61K 31/5415 514/224.8 |
| 2015/0335740 A1* | 11/2015 | Lo | A61K 45/06 514/789 |

* cited by examiner

*Primary Examiner* — Dominic Lazaro

(57) ABSTRACT

A method for administering solid water particles to prevent bacteria growth in living organisms utilizes a solid water particle (SWP) solution to attract and kill a bacterium through polarization. The method inhibits growth of a bacterium or an enveloped virus with an inorganic solution comprised substantially of SWP. The SWP kill the bacterium by providing a solution comprised substantially of SWP having inherent dipole characteristics that generate an electric field. The generated electric field attracts a bacterium to the SWP. Once engaged, the bacterium cannot move. The electric field also creates sufficient internal pressure in the bacterium, which bursts the cell walls of the bacterium, thereby killing bacterium. This mechanism also kills superbug, which are drug resistant bacteria. The method is also efficacious for killing enveloped viruses in the same manner. Further, administering the SWP solution into the mouth for a duration, helps reduce tooth pain and treat periodontal diseases.

13 Claims, 8 Drawing Sheets

100

102 Providing a solution of solid water particles, the solid water particles defined by a positive dipole operable to generate an electric field

104 Administering the solution of solid water particles on an affected area having a bacterium

106 Inducing, through the electric field, polarization of the bacterium

108 Whereby the bacterium is electrically drawn to the solid water particles

110 Whereby the polarization generates an internal pressure in the bacterium

112 Whereby the cell walls of the bacterium are destroyed by the internal pressure

FIG. 1

METHOD FOR ADMINISTERING SOLID WATER PARTICLES TO PREVENT BACTERIA GROWTH IN LIVING ORGANISMS

CROSS REFERENCE OF RELATED APPLICATIONS

This application claims the benefits of U.S. provisional application No. 62/836,940, filed Apr. 22, 2019 and entitled a METHOD FOR INHIBITING GROWTH OF BACTERIA, SUPERBUG AND VIRUS WITH SOLID WATER PARTICLES, which provisional application is incorporated by reference herein in its entirety.

FIELD OF THE INVENTION

The present invention relates generally to a method for administering solid water particles to prevent bacteria growth in living organisms. More so, the present invention relates to a method that leverages the dipole properties of solid water particles (SWP) to capture and kill bacterium through oral and topical administration thereof.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Typically, solid water particles consist of numerous molecules, which are comprised of two hydrogens and one oxygen, clustering together. The solid water particle is a new solid state of water that does not melt at room temperature and pressure, so as to avoid the implication of a liquid state. It is well known that even distilled water will grow bacteria after some time. This occurs because seeds of algae may contaminate the distilled water. With water, some light, and a small amount of dissolved carbon dioxide, algae can photosynthesize and multiply. Algae may then become the food for bacteria to grow.

Generally, solid water particles exhibit unique dipole electrical properties, generating an electric field. The electric field is stronger for smaller clusters of solid water particle, and weaker for larger clusters of solid water particle, due to the negating effects of greater number of solid water particles. However, the smaller clusters of solid water particles having the larger electric fields are generally disposed at the outer regions of the solid water particle cluster, which enhances the polarizing effect thereof.

It is recognized that superbugs are bacteria that develop drug-resistant ability. Most current antibiotics disrupt the biochemical reactions of the bacteria. Specifically, they inhibit DNA synthesis, RNA synthesis, cell wall synthesis, or protein synthesis of the bacteria. Superbugs do not develop electric-field resistant ability. As solid water particle kills bacteria with extremely high electric field, so it will kill and inhibit the growth of superbugs, which are resistant to current antibiotics.

Other proposals have involved anti-virus medical treatments and medical solutions. The problem with these treatments is that they do not utilize solid water particles. Also, the administration is not always possible through both oral and topical means. Even though the above cited anti-virus medical treatments meet some of the needs of the market, a method that leverages the dipole properties of solid water particles (SWP) to capture and kill bacterium through oral and topical administration thereof, is still desired.

SUMMARY

Illustrative embodiments of the disclosure are generally directed to a method for administering solid water particles to prevent bacteria growth in living organisms. The method leverages the dipole properties of solid water particles (SWP) to capture and kill bacterium through oral administration thereof. The dipole properties of the SWP generates an electric field that can be enhanced for drawing the bacterium to the SWP particle; and then creates internal pressure on the cell walls of the bacterium—killing the bacterium.

In some embodiments, the method provides discrete steps that include the utilization of a solution of SWP to attract and kill a bacterium through polarization. The method inhibits growth of a bacterium or an enveloped virus with an inorganic solution comprised substantially of SWP. The SWP kill the bacterium by providing a solution comprised substantially of SWP having inherent dipole characteristics that generate an electric field. The generated electric field attracts a bacterium to the SWP.

Once the SWP particle and bacterium are electrically engaged, escape/movement by the bacterium is restricted. The electric field also creates sufficient internal pressure in the bacterium, which bursts the cell walls of the bacterium, thereby killing bacterium. This mechanism also kills superbug, which are drug resistant bacteria. The method is also efficacious for killing enveloped viruses in the same manner. Further, administering the SWP solution into the mouth for a duration, reduces tooth pain, and treats periodontal diseases.

One aspect of the method for inhibiting growth of bacteria with solid water particles, comprises an initial Step of providing a solution of solid water particles, the solid water particles defined by a positive dipole operable to generate an electric field.

Another Step includes administering the solution of solid water particles on an affected area having a bacterium.

The method also includes a Step of inducing, through the electric field generated by the solid water particles, polarization of the bacterium.

A Step comprises, whereby the bacterium is electrically drawn to the solid water particles.

A further Step comprises, whereby the polarization generates an internal pressure in the bacterium.

A final Step comprises, whereby the cell walls of the bacterium are destroyed by the internal pressure.

In another aspect, the solution of solid water particles is operable to prevent the growth of a superbug.

In another aspect, the solution of solid water particles is operable to prevent growth of an enveloped virus.

In another aspect, the method is configured to inhibit bacteria growth in livestock, including: chickens, cows, sheep, and horses.

In another aspect, the solid water particle comprises a plurality of solid water particles that form a cluster.

In another aspect, the cluster of solid water particles is rod shaped.

In another aspect, the solid water particle is the solvent in the solution.

In another aspect, the solution of solid water particles is administered topically and orally.

In another aspect, the solution of solid water particles is operable to inhibit bacteria and virus growth in the mouth, gums, teeth, ears, nose, skin, eyes, penis, and vulva.

In another aspect, the solution of solid water particles reduces pain and inflammation of the teeth and oral cavity, caused by gingilis and periodontitis.

In another aspect, the solution of solid water particles reduces pain and inflammation in the gums and teeth, whereby the solution of solid water particles is held in the mouth for a duration.

In another aspect, the method also serves to enhance the dipol effect of the solid water particles by manipulating a magnet or a magnetic metamaterial between proximal and distal positions from the solution of solid water particles to further induce the generated electric field.

In another aspect, the method also serves to produce the solid water particles by: immersing a culture the bacterium in water with the solid water particles in suspension; drying the specimen of the bacterium on a copper grid that is used for a transmission electron microscope; and extracting a small specimen of the bacterium.

In another aspect, the solid water particle is an inorganic solution.

In another aspect, the inorganic solution is administered topically and orally.

In another aspect, the method is configured to inhibit bacteria growth in the mouth and eyes.

In another aspect, the method is configured to inhibit bacteria growth in livestock, such as chickens and cows.

One objective of the present invention is to kill bacteria, including superbugs, through dipolar interaction with solid water particles.

Another objective is to enhance the dipolar effect of the solid water particles on the bacterium through an external source, including a magnet.

Another objective is to inhibit growth of bacteria in the mouth and eyes.

Another objective is to provide an inorganic solution comprised chiefly of SWP to inhibit growth of bacteria.

Another objective is to provide an inexpensive anti-bacterial solution.

Another objective is to provide a method for administering solid water particles to prevent bacteria growth in living organisms that can be applied easily through topical or oral means known in the art.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIG. 1 illustrates a flowchart diagram of an exemplary method for administering solid water particles to prevent bacteria growth in living organisms, in accordance with an embodiment of the present invention;

FIG. 7A shows the teeth before treatment with an inorganic solution of solid water particles. FIG. 7B shows the teeth after treatment, in accordance with an embodiment of the present invention;

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

Figure 2:
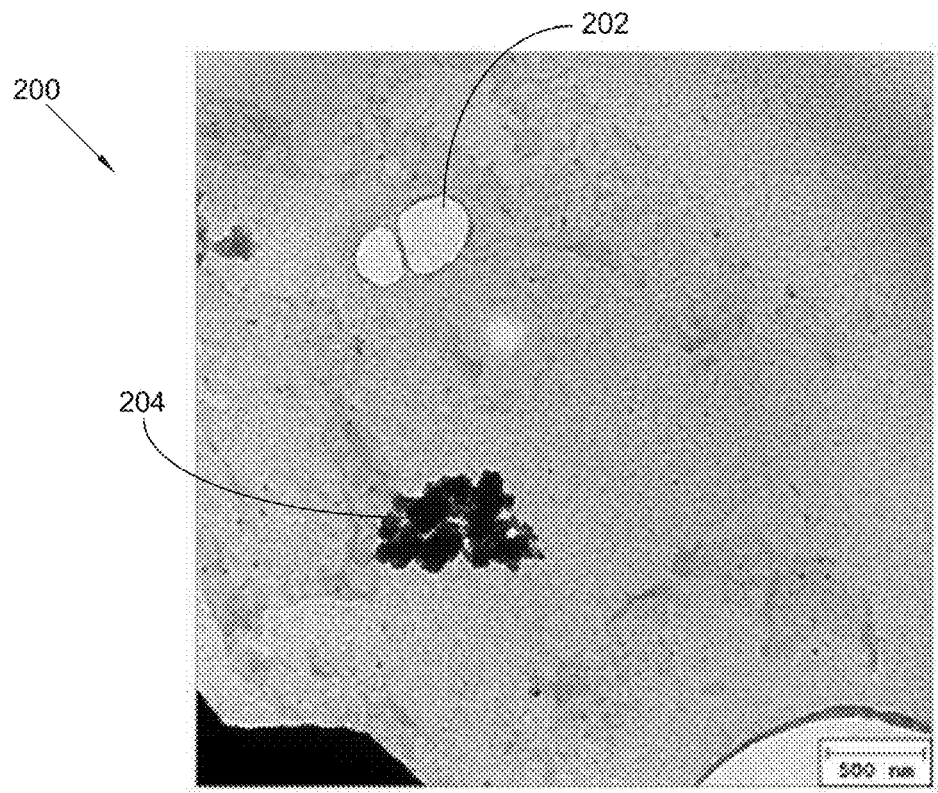
FIG. 2 illustrates a top view of a solid water particle cluster and an *E. coli* bacterium, in accordance with an embodiment of the present invention under a transmission electron microscope.
Figure 3:
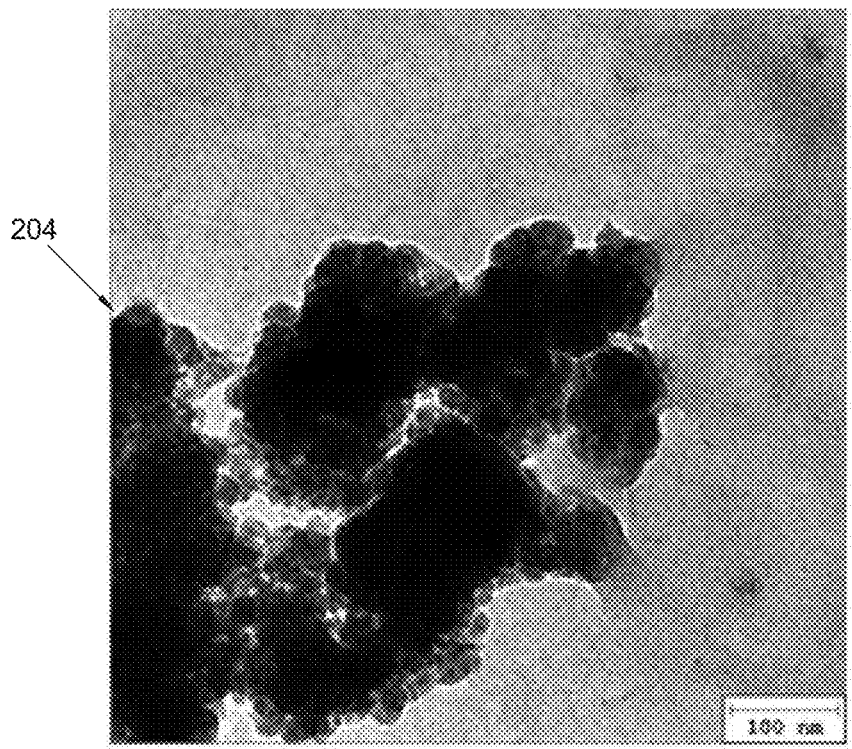
FIG. 3 illustrates an enlarged view of the bacterium shown in FIG. 2, under a transmission electron microscope, in accordance with an embodiment of the present invention.
Figure 4:
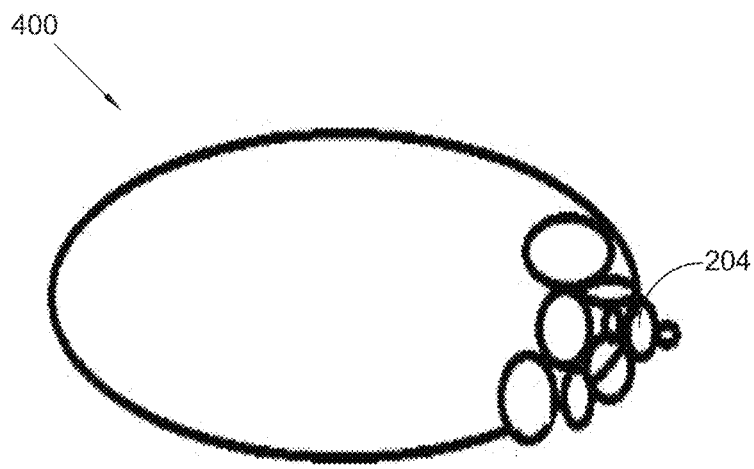
FIG. 4 illustrates a closeup view of the internal structure of a micron size rod shaped solid water particle cluster, in accordance with an embodiment of the present invention.
Figure 5:
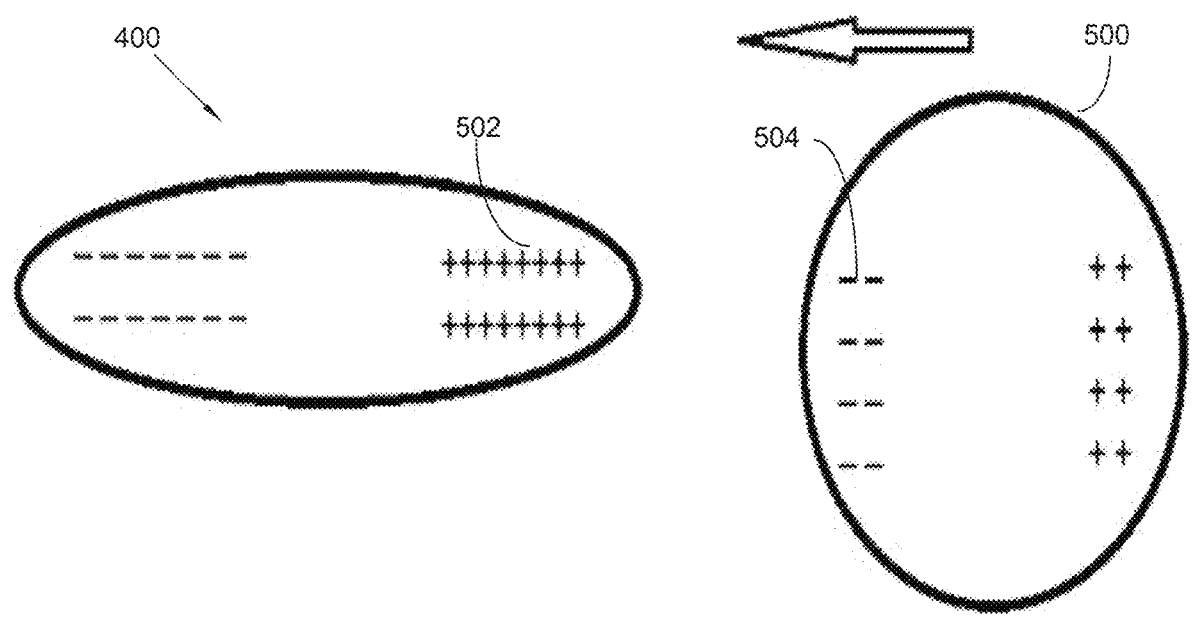
FIG. 5 illustrates a graphic representation of the induced polarization of the bacterium by the rod-shaped solid water particle cluster shown in FIG. 4, in accordance with an embodiment of the present invention.
Figure 6:
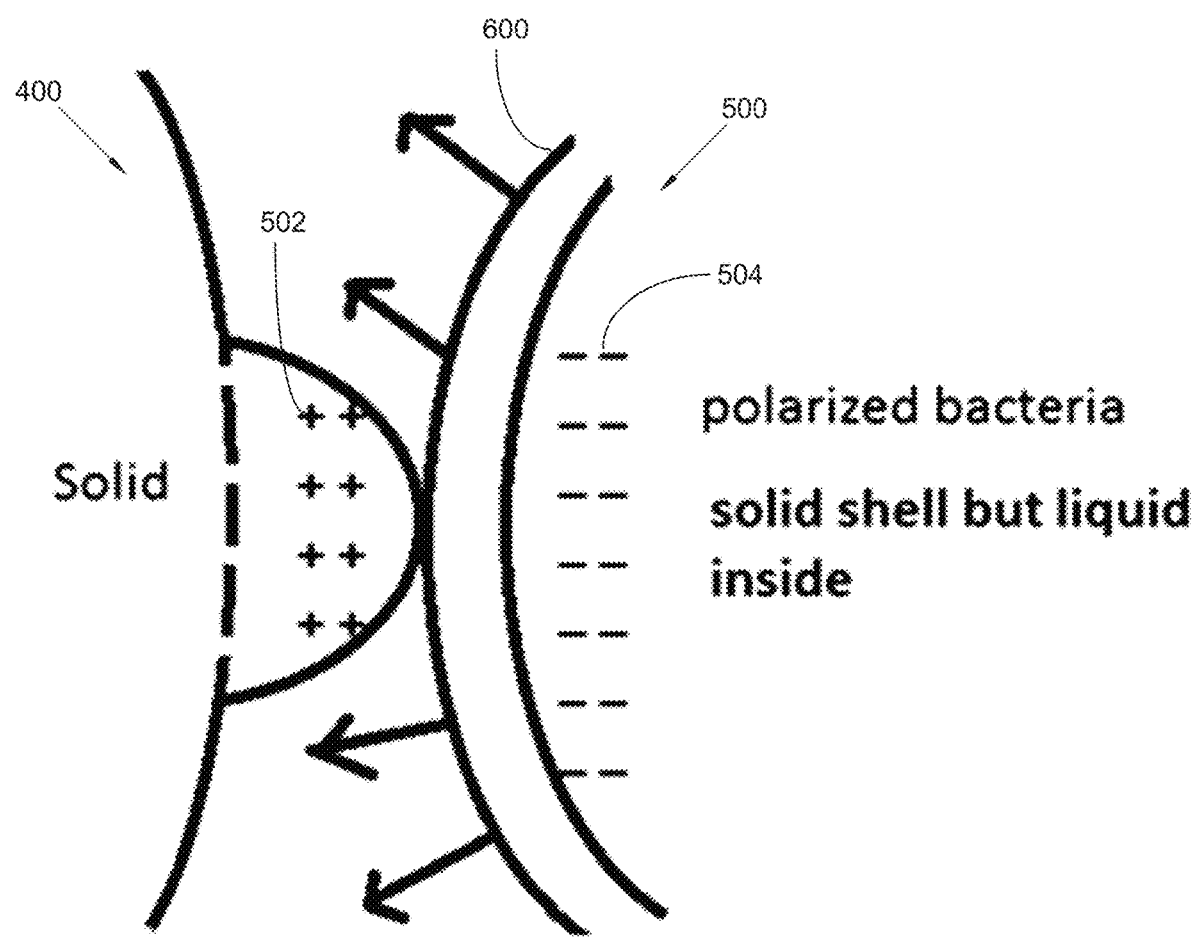
FIG. 6 illustrates a graphical representation of the bacterium shown in FIG. 5 bursting after engaging the rod-shaped solid water particle cluster, in accordance with an embodiment of the present invention.
Figure 7A:
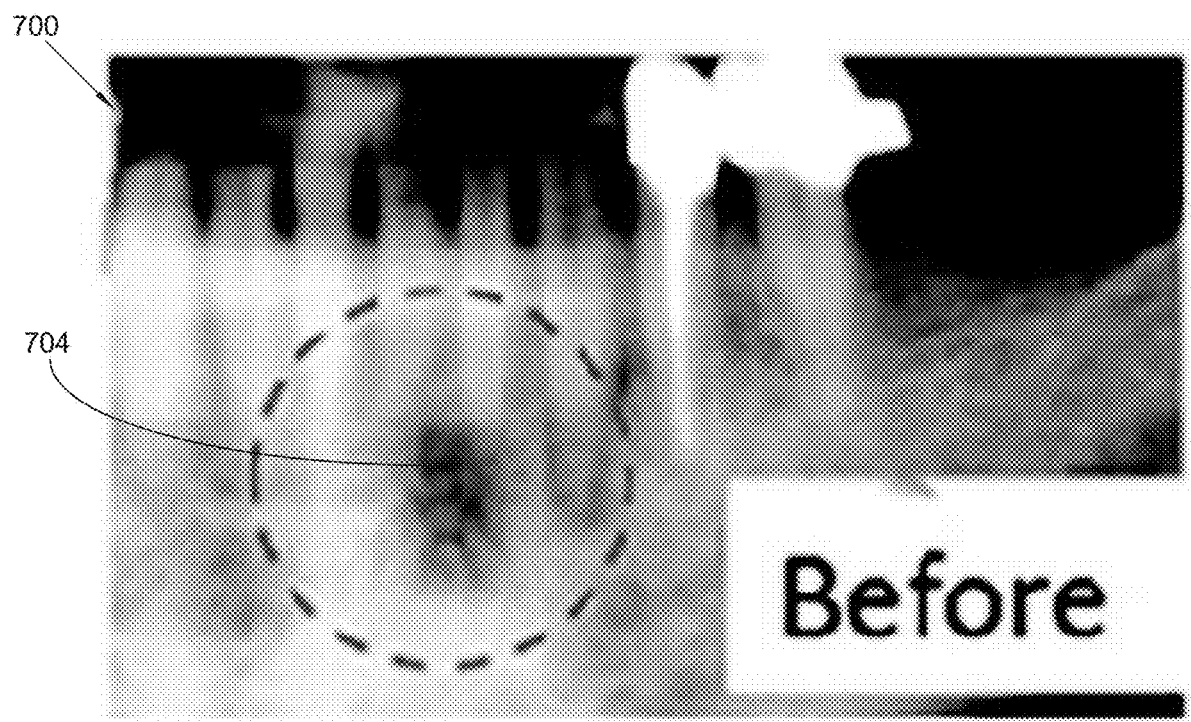
FIGS. 7A and 7B illustrate an X-ray image of teeth from an individual suffering from gum and tooth decay, where
Figure 7B:
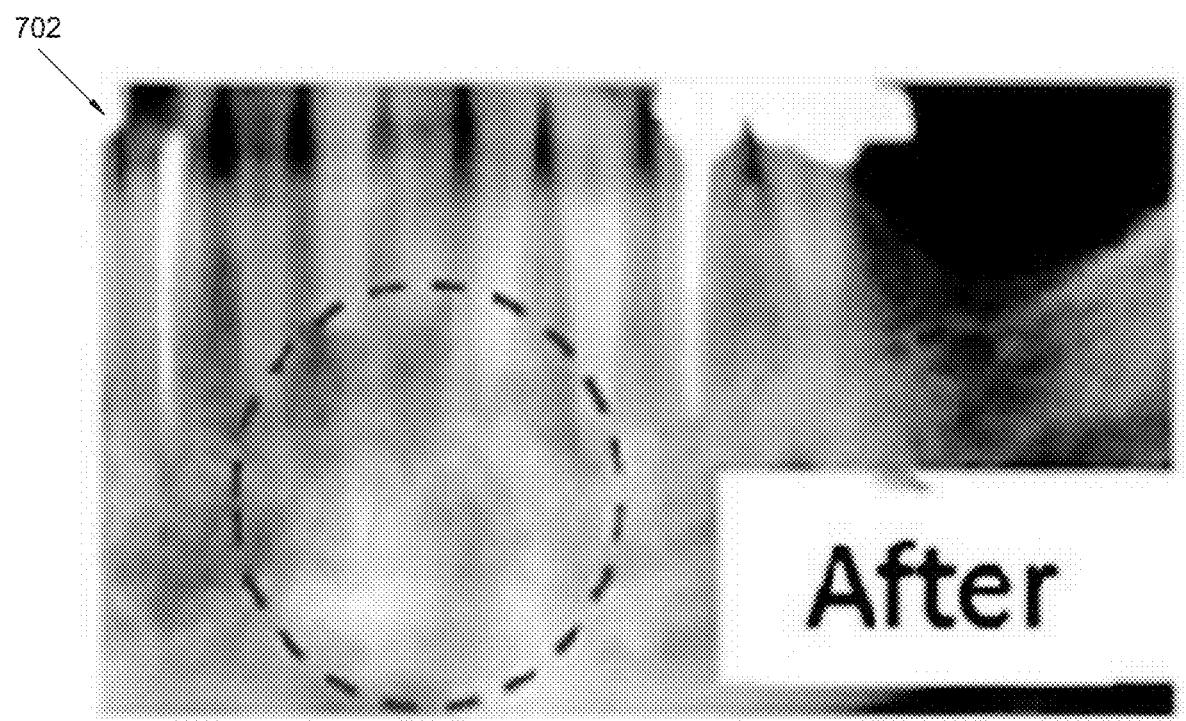
Figure 8:
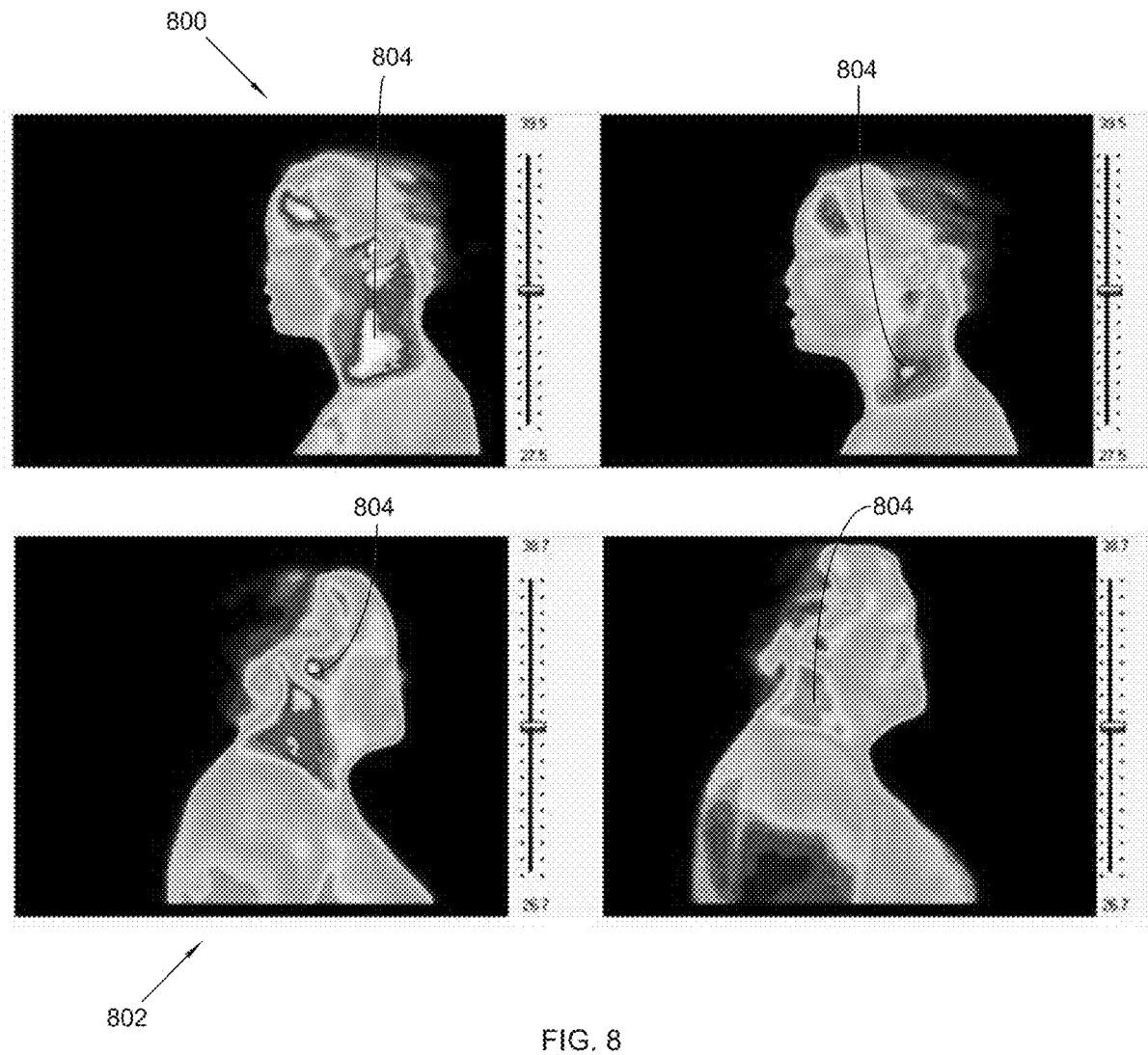
FIG. 8 illustrates a comparison between two thermograph images of two individuals, showing the hottest portions of the body are shown in white, with the color gradient going from red to blue to black from hot to cold, in accordance with an embodiment of the present invention.
Figure 9:
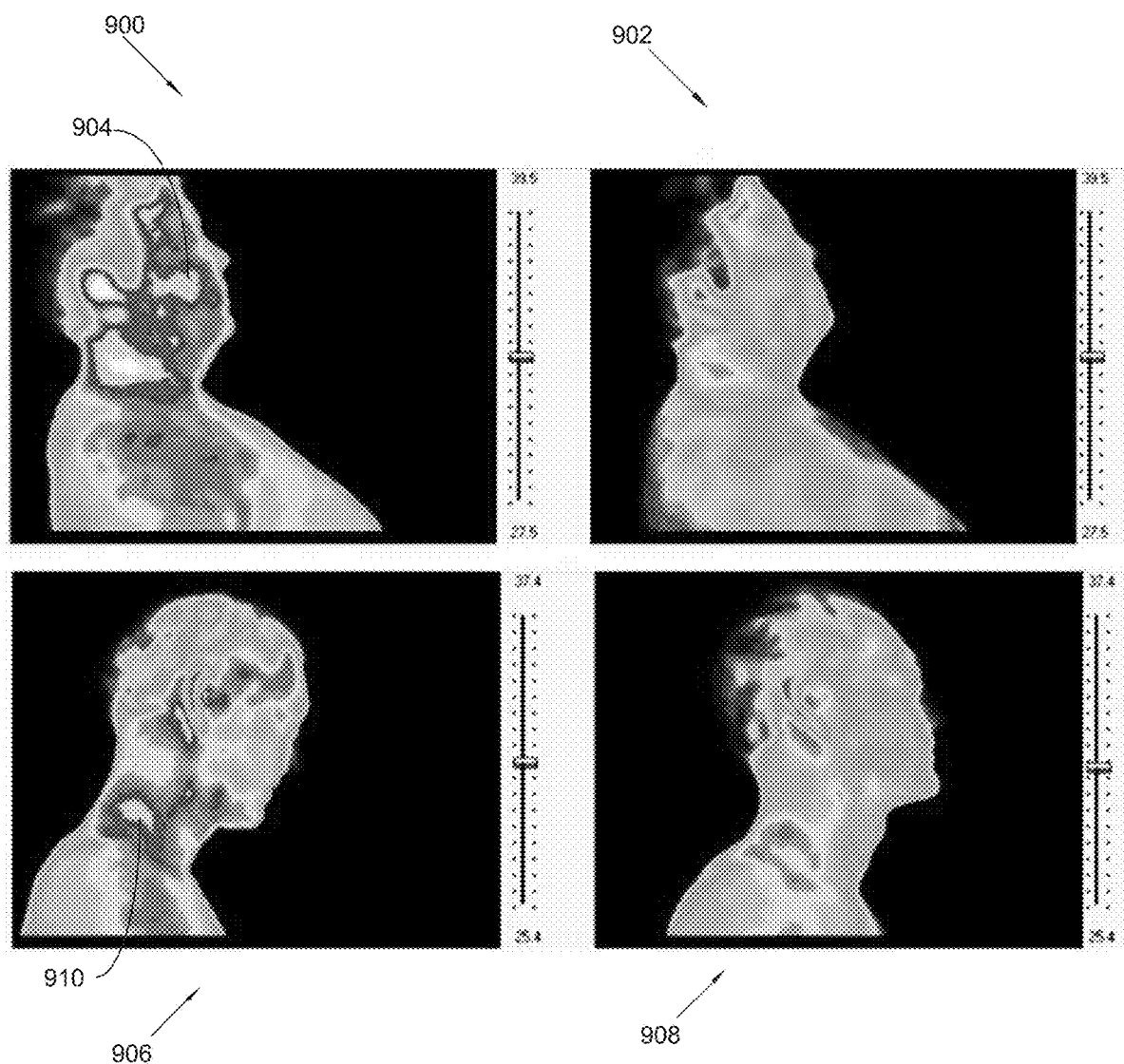
FIG. 9 illustrates exemplary before and after thermograph images of a body suffering from tooth problems, in accordance with an embodiment of the present invention.
Figure 10:
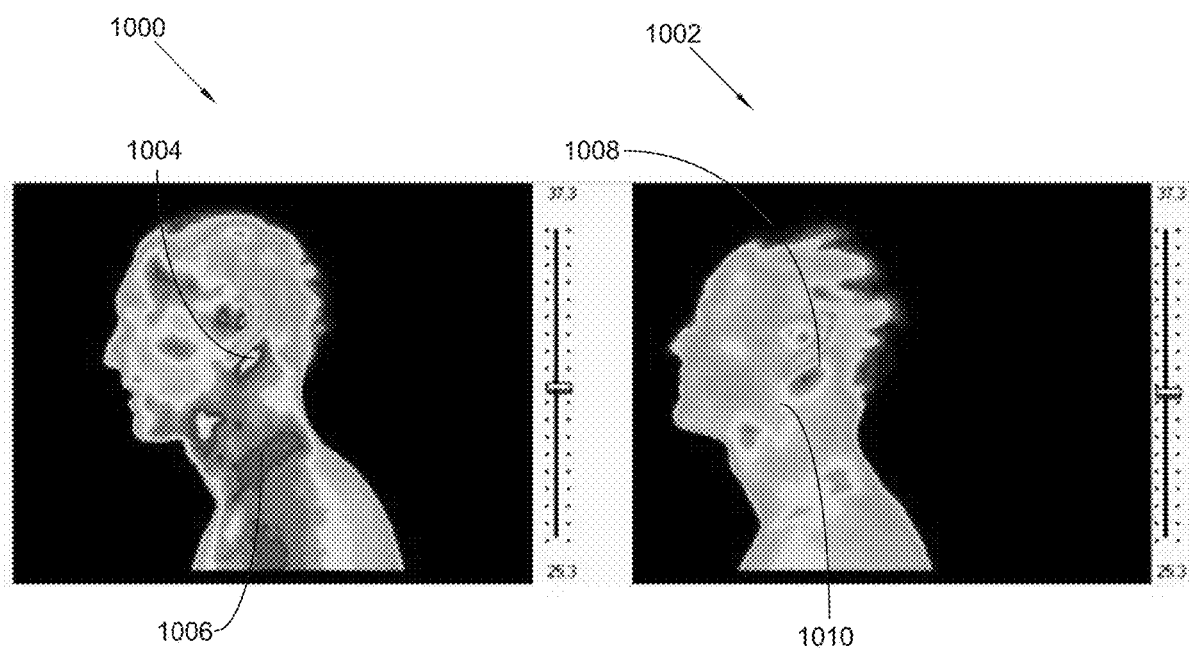
FIG. 10 illustrates thermograph images of an individual similar to FIG. 9, with red hot spots and white-hot spots indicating bacterial inflammation, in accordance with an embodiment of the present invention.

A method 100 for administering solid water particles to prevent bacteria growth in living organisms is referenced in FIGS. 1-10 The method 100 provides an efficient, non-invasive medical procedure for killing bacterium, including superbugs and other communicable viruses known in the art. The unique dipolar characteristics of solid water particles are applied to the bacterium to draw the bacterium into proximity or full engagement with the solid water particles; and then the electrical dipolar force naturally works to crush the cell walls of the bacterium. In some embodiments, the method provides steps for formulating a solution of the solid water particles. In other embodiments, the method provides steps for enhancing the dipolar effects from the solid water particles, so as to increase efficacy of killing the bacterium.

In one exemplary use, the method 100 provides a unique inorganic solution comprised substantially of solid water particles that form solid water particle clusters 202. The solid water particle clusters 202 have sufficient polarity to induce a strong electric field. The electric field is effective for polarizing, attracting, and killing a bacterium 204. Further, the method 100 is unique in that a solution of the solid water particles is operable to prevent the growth of a superbug and/or an enveloped virus. Those skilled in the art will recognize that superbugs are bacteria that develop drug-resistant ability. Most current antibiotics disrupt the biochemical reactions of the bacteria. Specifically, they inhibit DNA synthesis, RNA synthesis, cell wall synthesis, or protein synthesis of the bacteria. Superbugs do not develop electric-field resistant ability. As SWP kills bacteria with extremely high electric field., so it will kill and inhibit the growth of superbugs, which are resistant to current antibiotics. The method 100 is also efficacious for preventing bacteria growth in livestock, such as, chickens, cows, sheep, and horses.

A flowchart diagram for an exemplary method 100 for administering solid water particles to prevent bacteria growth in living organisms, is referenced in FIG. 1. The steps described in the method 100 are exemplary, and may include additional steps; or may be operable with less steps than described. The order/sequence of the steps may be randomly applied, as required for treating different types of viruses, bacteria, fungi, and the like.

The method 100 works to prevent growth of bacteria through use of a solution of solid water particles, with the method 100 comprising an initial Step 102 of providing a solution of solid water particles, the solid water particles defined by an electric dipole operable to generate an electric field. In some embodiments, the solid water particle comprises a plurality of solid water particles that form a cluster. The cluster may be rod-shaped. And the solid water particle is the solvent in the solution. In one non-limiting embodiment, the solution of solid water particles comprises an inorganic solution. The inorganic solution is administered topically and orally.

The production of the solid water particles is also taught in the method 100. This may include the steps of immersing a culture the bacterium in water with the solid water particles in suspension.

It is known in the art that multiple SWPs form a cluster having a generally curved rod shape. FIG. 2 illustrates an image 200 of an exemplary SWP cluster 202 and a bacterium 204. The image is shown at a scale of 500 nm. On the lower region of the image 200, a faint image of a curved rod appears. This represents the SWP cluster 202. The mass of dark broken pieces adjacent to the SWP cluster 202 represents the bursting of a cell wall 600 of the bacterium 204, and specifically an *E. coli* bacterium. FIG. 3 illustrates a five-time enlargement of the bacterium 204 shown in FIG. 2. The scale of the bacterium 204 in FIG. 3 is about 100 nm, which allows the broken pieces of the *E. coli* bacteria to be more visible.

The SWP cluster 202, like the individual SWPs, has a positive dipole 502. The positive dipole 502 generates a strong electric field that works to attract and create internal pressure in objects, such as a bacterium 204. In some embodiments, the SWP cluster 202 generates an electric dipole. The electric dipole 502 emits a strong electric field that is effective in polarizing surrounding objects, and especially objects having a negative dipole 504. Those skilled in the art will recognize that the electric field is stronger for smaller clusters of SWP, and weaker for larger clusters of SWP, due to the negating effects of greater number of SWPs. However, the smaller clusters of SWPs having the larger electric fields are generally disposed at the outer regions of the SWP cluster 202, which enhances the polarizing effect thereof.

In some embodiments, the emitted electric field is efficacious for attracting the bacterium 204 to the SWP cluster 202. Specifically, the water inside a cell wall 600 of the bacterium 204 is induced into polarization to attract to the bacterium 500. The bacterium 500 that is attracted is generally proximal to the SWP cluster 202. Once engaged with the SWP cluster 202, the strong electrical field restricts the bacterium 204 from disengaging therefrom.

Further, the electric field creates an internal pressure in the bacterium 204. The internal pressure increases inside the cell wall 600 of the bacterium 204 until reaching a critical point that kills, or bursts, the bacterium 204. This is because the cell wall 600 of the bacterium cannot withstand excessive pressure. Also, the outer surface of the SWP cluster is generally rigid relative to the cell wall 600.

The SWP is made up of many molecules, which are comprised of two hydrogens and one oxygen, clustering together. Those skilled in the art will recognize that SWP is a new solid state of water that does not melt at room temperature and pressure, so as to avoid the implication of a liquid state. It is well known that even distilled water will grow bacteria after some time. This occurs because seeds of algae may contaminate the distilled water. With water, some light, and a small amount of dissolved carbon dioxide, algae can photosynthesize and multiply. Algae may then become the food for bacteria to grow.

The micron size rod of SWP cluster 202 shown in FIG. 2 consists of a smaller SWP which is around several hundred nanometers. The hundred nanometers sized SWP in turn consists of 30 to 50 nanometer SWP. FIG. 4 illustrates the internal structure of a micron size rod shaped SWP cluster 400. The rod shaped SWP cluster 400 is made up of hundreds of nanometers in size, which in turn is made up of smaller ones that are in the tens of nanometers in size.

Another Step 104 includes administering the solution of solid water particles on an affected area having a bacterium. The inorganic solution of SWP may be administered topically or orally. In one experimental embodiment, drinking and dropping the inorganic solution of SWP into the eyes has an inflammatory effect. In some embodiments, the solution of solid water particles is administered topically and orally. In this manner, the solution of solid water particles is operable to inhibit bacteria and virus growth in the mouth, gums, teeth, ears, nose, skin, eyes, penis, and vulva. For example, FIGS. 7A and 7B illustrate an X-ray image of teeth from an individual suffering from gum and tooth decay, where FIG. 7A shows the teeth before treatment with an inorganic solution of solid water particles. FIG. 7B shows the teeth after treatment.

Further, the solution of solid water particles reduces pain and inflammation of the teeth and oral cavity, caused by gingilis and periodontitis. The solution of solid water particles reduces pain and inflammation in the gums and teeth, whereby the solution of solid water particles is held in the mouth for a duration. The inorganic solution of SWP may be administered topically or orally. In one experimental embodiment, drinking and dropping the inorganic solution of SWP into the eyes has an inflammatory effect.

The method 100 also comprise a Step 106 of inducing, through the electric field generated by the solid water particles, polarization of the bacterium. It is known in the art that when an SWP cluster 202 is first created, it is small, but has very strong electric field. Smaller SWP clusters combine to form bigger ones, which have comparatively smaller net strong electric field, because most of the electric field from the smaller ones are neutralized. The larger the SWP clusters, the smaller the electric field. The smallest SWP clusters that have the strongest electric field lie on the outer region of the rod are the ones that cause the explosion of the bacterium 204, and the death.

In another possible embodiment, a Step comprises manipulating a magnet or a magnetic metamaterial between proximal and distal positions from the solution of solid water particles to further induce the generated electric field. This can include swaying the magnet in front of the affected part of the body in which the solid water particles are administered. The dipole effect is increased, as the magnetic metamaterial or a magnet is moved away from the solid water particles. Those skilled in the art will recognize that dipole moment is a result of multiplication of the magnitude of charges (Q) and the distance between them. Thus, when a proton and electron get closer (bond length decreases), polarity decreases hence the dipole decreases. When they move further away from each other (bond length increases), the polarity increases and hence dipole moment increases. In one non-limiting embodiment, the magnetic metamaterial may include a silver nanostrip and a thick silver film.

FIG. 6 illustrates a graphical representation of the bacterium 500 shown in FIG. 5 bursting after engaging a rod shaped SWP cluster 400. As shown in the FIG. 6, when the polarized bacterium 500 touches the rod shaped SWP cluster 400 and cannot move any further, the electrostatic attractive force builds up sufficient internal pressure to burst open the cell wall 600 of the bacterium 500.

The rod shaped SWP cluster 400 has an electric positive dipole 502 that emits a strong electric field. The bacterium 500 has an electric dipole 504. The electric field generated by the positive dipole 502 works to polarize the bacteria in the proximal area of the SWP cluster 400, and attract the bacterium 500. As the bacterium 500 is attracted at increasing speed towards the SWP cluster 400, the bacterium 500 eventually engages the SWP cluster 400.

The surface of the SWP cluster is generally solid and rigid relative to the bacterium 500. On the surface of the SWP cluster 400, the smallest rod is 30 to 50 nanometer in size. The SWP cluster 400 is generally solid, and bacterium 500 bursts upon engaging this rigid surface, as shown in FIGS. 2 and 3.

A further Step 110 of the method 100 comprises, whereby the polarization generates an internal pressure in the bacterium. The SWP clusters are operable to generate a strong electric field that emits from its aligned electric dipole moment of its water molecules. This strong electric field will polarize any bacteria which happens to be near. The dipoles of water molecules inside the bacteria will be realigned along the strong electric field from SWP. The bacteria will become strongly polarized with a very large electric dipole moment.

This is shown in FIG. 5, which shows a graphic representation of the induced polarization of the bacterium 500 by the rod shaped SWP cluster 400 shown in FIG. 4. The thin oval structure on the left is the rod shaped SWP cluster 400. The positive dipole 502 shows the partial positive charge is on the right. The bacterium 500 is attracted to the dipole of the rod shaped SWP cluster 400 because of the induced polarization of the water inside the cell.

Thus, the electric potential energy U between two electric dipoles is:

$$U=-p_s \cdot p_b/(4\pi\varepsilon r^3)$$

Where $p_s$ is the electric dipole moment of the SWP cluster 400, $p_b$ the induced electric dipole moment of the bacteria, ε the dielectric constant of vacuum, and r is the distance between the SWP cluster 400 and the bacterium 500. As the bacterium 500 gets closer to SWP cluster 400, it sees a stronger electric field from the SWP cluster 400. Inside the effective small volume of SWP that finally touches the bacterium 500, the electric dipoles of all water molecules is assumed to be lined up. So the total effective electric dipole moment of SWP cluster 400 becomes $$P_s=N_s p_0,$$

where $N_s$ is the effective number of water molecules that line up inside the effective volume of SWP cluster 400. To a first order approximation the bacterium 500 could be regarded as consisting of water molecules, so the induced electric dipole moment of the bacterium 500 becomes:

$$P_b=N_b p_0$$

where $N_b$ is the effective number of water molecules inside the bacterium 500. After the bacteria and the SWP cluster 400 engage, the shortest effective distance becomes d. Let the electric dipole moment be given by $$P_0=ed_0,$$

where do is the size of the water molecule. The internal pressure $P_b$ inside the bacterium 500 near the SWC cluster 400 is equal to the electric energy per unit volume:

$$P_b-U/V,$$

The effective volume of the bacterium 500 is shown in FIG. 6 as approximately $$V=(d/2)^3$$

The number of effective water molecules with electric dipoles lined up in SWP clusters 400 and bacterium 500 become:

$$N_s=(d/d_0)^3/8$$

$$N_b=(d/d_0)^3/8$$

Then the pressure inside the bacterium 500 becomes:

$$\begin{aligned} P_b &= U/d^3 \\ &= U_0/(64\,d_0^3) \end{aligned}$$

where $U_0$ is the electric energy of one water molecule due to its own dipole:

$$U_0=e^2/(4\pi\varepsilon_0 d_0)$$

Putting in the numerical value for the size of water molecule $d_0$ to be 0.3 nm, we get $U_0$ to be 2.4 eV. The internal pressure inside the bacterium 500 becomes approximately $P_b$=2,220 atmospheric pressure, which is huge, and can easily burst the cell wall of the bacteria and causes it to die.

A final Step 112 of the method 100 comprises, whereby the cell walls of the bacterium are destroyed by the internal pressure. Generally, the cell walls 502 of the bacterium 500 burst under the internal pressure. The bursting of bacterium 500 is caused by a physical mechanism. The death of the bacterium 500 is immediate.

The administration of the solution of solid water particles is key to the efficacy. Thus, the method 100 is administered orally and to the eyes to inhibit growth of bacteria. Experimentally, the method 100 provides evidence of antibacterial action in humans. In addition, the antibacterial action is evident in tooth decay that occurs in the human mouth. For example, FIGS. 7A and 7B illustrate X-ray images 700, 702 of teeth from an individual suffering from gum and tooth decay. The image 700 of FIG. 7A shows the teeth before treatment with SWP. The image 702 of FIG. 7B shows the teeth after treatment. As can be seen, image 700 displays tooth decay evident by a darkened portion 704 that has been circled. The bottom image shows a lack of this decay evidencing repair.

In FIG. 7A, the X-ray image of the teeth show the decay state of the gum and teeth. After applying the SWP for several days, gum and tooth repair occurs as shown in the FIG. 7B X-ray image 702. In yet another example, evidence of antibacterial action is visible through thermographs. An experiment was conducted by taking a set of thermal images of the left and right side of the head; asking the individual to drink an 2 ounce of the inorganic solution of SWP; waiting 15 minutes; taking another set of thermal images of the left and right side of the head; and comparing before and after pictures.

If the SWP produced no effect, there would be no change in temperature. If the SWP had an effect, there were changes in temperature. As a control, FIG. 8 illustrates a woman who has no tooth problem, and hence no inflammation shown on the cheek. There is no change in temperature distribution of the cheek before after drinking the inorganic solution of SWP.

Looking again at FIG. 8, the thermograph images of two control subjects 800 and 802 of with no dental problems is shown. The two left hand side images are images of these two individuals before drinking solutions with solid water particles. The two right hand side images are images of these two individuals after drinking solutions with solid water particles. The color code of the thermograph is as follows: the hottest portions of the body are shown in white spots 804, with the color gradient going from red to blue to black from hot to cold.

As illustrated, there are no white spots or even red area in the mouth area, and there is no change of temperature before and after drinking solution with solid water particles. This indicates that there is no dental problem for these two individuals 800 and 802. For comparison we show hottest area 804, shown in white area in neck area (upper images), and ear area (lower images), cool down from drinking solution with solid water particles, change in size and color from drinking solution with solid water particles.

Turning to FIG. 9, an exemplary thermal image showing the before and after thermograph images 900, 902 of a woman suffering from tooth problems. The top thermographs are the before and after (left and right respectively) of the woman with dental problems. As can be seen in the thermograph images, there are two white spots 904 on the left indicating inflammation, chiefly from bacteria. After drinking the inorganic solution of SWP, the temperature and inflammation of the individual went down in image 902.

The bottom images 906, 908 are of a man suffering from tooth problems. Similar to the top pictures, the man's tooth problems are evidenced by one white spot and one red spot 910 on the before image 906. After drinking the solution of SWP, or holding the solution for a period of time in the mouth, the temperature also decreased, as evidenced in the after image 908.

Thus, FIG. 9 illustrates graphically the teeth problems on the left side of the mouth cavity of the woman 900, 902, and the man 906, 908. The serious bacterial issues are shown in either white dot 904 or red dot 910. After drinking the solution of SWP, the white and red dots 904, 910 vanish, indicating the inflammation caused by the bacteria has subsided, which can be used as evidence that the bacteria in the teeth decay have been killed.

FIG. 10 illustrates thermograph images 1000, 1002 of an individual similar to FIG. 9, The left image 1000 is a thermograph of an individual with a dental problem. The hot spots can be seen as white spots 1004 and red spots 1006, indicating bacterial inflammation. About 15 minutes after treatment the right thermograph reveals that temperature and inflammation is reduced. In FIG. 10, the teeth and gum problems of the mouth cavity on the right side are shown as a white spot 1004 and red spot 1006. After drinking the inorganic solution of SWP, the temperature decreases to become a red spot 1008 and pale-yellow area 1010. This is evidence that inflammation caused by the bacteria has subsided, or that the majority of the bacteria has been killed.

In some embodiments, the method 100 provides numerous means for administering the SWP inorganic solution. For example, the SWP inorganic solution can be used to substitute antibiotics where they are used currently. As SWP has the ability to kill bacteria, it may be applicable in food preservation. The food can be any solid food such as animal feed. The food can be any liquid such as oil of any kind, such as olive oil, flexi oil, any cooking oil.

Superbugs are bacteria that develop drug-resistant ability. Most current antibiotics disrupt the biochemical reactions of the bacteria. Specifically, they inhibit DNA synthesis, RNA synthesis, cell wall synthesis, or protein synthesis of the bacteria. Superbugs do not develop electric-field resistant ability. As SWP kills bacteria with extremely high electric field., so it will kill and inhibit the growth of superbugs, which are resistant to current antibiotics.

As discussed above, the method 100 is effective for killing organisms, beyond bacteria. In one embodiment, the method 100 is applicable on animals and plants to kill bacteria. In another embodiment, the method 100 works substantially the same for killing viruses that are enclosed within a membrane, i.e., an enveloped virus. The SWP attracts these viruses to its surface. Upon touching the SWP, the membrane, or the envelope of the virus immediately bursts and dies.

As shown below, the classes of Enveloped Viruses that contain Human Pathogens may include, without limitation:

A: DNA viruses, Herpes viruses, Poxviruses, Hepadnaviruses

B: RNA viruses, such as HIV, Flavivirus, Toga virus, Coronavirus, Hepatitis D, Orthomyxovirus, Paramyxovirus, Rhabdovirus, Bunya virus, Filo virus, valiola C: Retroviruses and Hepadnavirus.

In conclusion, the method 100 for administering solid water particles to prevent bacteria growth in living organisms utilizes a solid water particle (SWP) solution to attract and kill a bacterium through polarization. The method inhibits growth of a bacterium or an enveloped virus with an inorganic solution comprised substantially of SWP. The SWP kill the bacterium by providing a solution comprised substantially of SWP having inherent dipole characteristics that generate an electric field.

Further, the electric field generated by the SWP attracts the bacterium. Once engaged, the bacterium cannot move. The electric field also creates sufficient internal pressure in the bacterium, which bursts the cell walls of the bacterium, thereby killing bacterium. This mechanism also kills superbug, which are drug resistant bacteria. The method is also efficacious for killing enveloped viruses in the same manner. Further, administering the SWP solution into the mouth for a duration, helps reduce tooth pain and treat periodontal diseases These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method of applying solid water particles to physically kill superbugs or enveloped viruses in living organisms, the method comprising:
   providing a solution of solid water particles, the solid water particles defined by an electrical dipole operable to generate an electric field;
   administering the solution of solid water particles on an affected area having superbugs or enveloped viruses, wherein the solution of solid water particles has larger clusters of solid water particles and smaller clusters of solid water particles, wherein the smaller clusters of solid water particles are disposed at the outer regions of the larger clusters of solid water particles;
   inducing, through the electric field generated by the solid water particles, polarization of the superbugs or the enveloped viruses;
   electrically drawing the superbugs or the enveloped viruses to the solid water particles;
   generating an internal pressure from the polarization of the solid water particles to the superbugs or the enveloped viruses; and
   destroying the cell walls of the superbugs or the enveloped viruses by the internal pressure.

2. The method of claim 1, wherein the method is configured to inhibit bacteria growth in livestock.

3. The method of claim 2, wherein the livestock includes at least one member selected from the group consisting of: cows.

4. The method of claim 1, wherein the solid water particle comprises a plurality of solid water particles that form a cluster.

5. The method of claim 1, wherein the cluster of solid water particles is rod shaped.

6. The method of claim 1, wherein the solid water particles are a solvent in the solution.

7. The method of claim 1, wherein the solution of solid water particles is administered topically and orally.

8. The method of claim 1, wherein the solution of solid water particles is operable to inhibit bacteria and virus growth in the mouth, gums, teeth, ears, nose, skin, eyes, penis, and vulva.

9. The method of claim 8, wherein the solution of solid water particles reduces pain and inflammation of the teeth and oral cavity, caused by gingilis and periodontitis.

10. The method of claim 8, wherein the solution of solid water particles reduces pain and inflammation in the gums and teeth, whereby the solution of solid water particles is held in the mouth for a duration.

11. A method of applying solid water particles to physically kill superbugs or enveloped viruses, the method comprising:
    providing a solution of solid water particles, wherein the solution of solid water particles has larger clusters of solid water particles and smaller clusters of solid water particles, and the smaller clusters of solid water particles are disposed at the outer regions of the larger clusters of solid water particles;
    administering the solution of solid water particles orally to an affected area having superbugs or enveloped viruses.

12. The method of claim 11, wherein the solid water particles are defined by a positive dipole operable to generate an electric field, the solid water particles comprising a plurality of solid water particles that form a rod-shaped cluster.

13. The method of claim 12, wherein the method comprises:
    inducing, through the electric field generated by the solid water particles, polarization of superbugs or enveloped viruses;
        whereby the superbugs or the enveloped viruses are drawn to the solid water particles;
        whereby the polarization generates an internal pressure in the superbugs or the enveloped viruses; and
        whereby the cell walls of the superbugs or the enveloped viruses are destroyed by the internal pressure.

* * * * *